United States Patent
Findley et al.

(10) Patent No.: US 6,475,729 B1
(45) Date of Patent: Nov. 5, 2002

(54) NUCLEIC ACID AMPLIFICATION AND DETECTION METHODS USING RAPID POLYMERASE CHAIN REACTION CYCLE

(75) Inventors: John Bruce Findley, Rochester; John Wesley Backus, Williamson; William Harold Donish; John William H. Sutherland, both of Rochester, all of NY (US)

(73) Assignee: Johnson & Johnson Clinical Diagnostics, Inc., Rochester, NY (US)

( * ) Notice: Subject to any disclaimer, the term of this patent is extended or adjusted under 35 U.S.C. 154(b) by 0 days.

(21) Appl. No.: 09/430,256

(22) Filed: Oct. 29, 1999

Related U.S. Application Data

(63) Continuation of application No. 07/693,574, filed on Apr. 30, 1991, now abandoned.

(51) Int. Cl.$^7$ .................................................. C12Q 1/68
(52) U.S. Cl. .......................................... 435/6; 435/91.2
(58) Field of Search ............................ 435/91.2, 6

(56) References Cited

U.S. PATENT DOCUMENTS

| | | | |
|---|---|---|---|
| 3,825,410 A | 7/1974 | Bagshawe ................ | 23/230 |
| 3,888,629 A | 6/1975 | Bagshaw ................... | 23/230 |
| 3,970,429 A | 7/1976 | Updike ...................... | 23/230 |
| 4,038,030 A | 7/1977 | Albright et al. .......... | 23/230 |
| 4,066,412 A | 1/1978 | Johnson et al. ............ | 23/243 |
| 4,089,747 A | 5/1978 | Bruschi ..................... | 195/99 |
| 4,446,232 A | 5/1984 | Liotta .......................... | 33/54 |
| 4,473,739 A | 9/1984 | Scheiwe et al. .......... | 219/302 |
| 4,683,195 A | 7/1987 | Mullis et al. ............... | 435/6 |
| 4,683,202 A | 7/1987 | Mullis ........................ | 435/91 |
| 4,713,326 A | 12/1987 | Dattagupta et al. ........ | 435/6 |
| 4,795,698 A | 1/1989 | Owen et al. ................. | 435/4 |
| 4,889,818 A | * 12/1989 | Gelfand et al. ............ | 435/194 |
| 4,902,624 A | 2/1990 | Columbus et al. ......... | 435/316 |
| 4,914,210 A | 4/1990 | Levenson et al. ......... | 548/413 |
| 4,920,061 A | 4/1990 | Poynton et al. ............ | 436/526 |
| 4,921,677 A | 5/1990 | Hinckley et al. .......... | 422/103 |
| 4,962,029 A | 10/1990 | Levenson et al. .......... | 435/192 |
| 4,964,188 A | 10/1990 | Olsen ........................ | 15/227 |
| 5,024,935 A | 6/1991 | McClune et al. ........... | 33/53 |
| 5,089,233 A | 2/1992 | DeVanney, Jr. et al. ..... | 422/99 |
| 5,195,305 A | 3/1993 | Findley et al. ............ | 435/6 |
| 5,270,183 A | * 12/1993 | Corbett et al. ............ | 435/91.2 |
| 5,460,780 A | 10/1995 | Devaney, Jr. et al. ....... | 422/99 |

FOREIGN PATENT DOCUMENTS

| | | | | |
|---|---|---|---|---|
| EP | 070 687 | 1/1983 | ................ | 33/58 |
| EP | 0 236 069 B1 | 9/1987 | ................ | 23/19 |
| EP | 402994 B1 | 12/1989 | | |
| EP | 402995 B1 | 12/1989 | | |
| EP | 0 370 694 A3 | 5/1990 | ................ | 33/543 |
| EP | 0 171 140 B1 | 8/1993 | | |
| EP | 0 393 744 B1 | 1/1995 | ................ | 19/34 |
| EP | 0 373 352 A2 | 1/1996 | ................ | 1/170 |
| EP | 0 373 352 B1 | 1/1996 | ................ | 1/170 |
| EP | 0 417 842 B1 | 10/1996 | ................ | 1/68 |
| EP | 0 408 735 B1 | 10/1997 | ................ | 9/38 |
| GB | 2 202 328 A | 9/1988 | ................ | 1/68 |
| WO | WO 88/01302 | 2/1988 | ................ | 1/68 |
| WO | WO A 89/07154 | 8/1989 | ................ | 1/68 |

OTHER PUBLICATIONS

Dodson et al. Molecular and Cellular Probes 5:21–25, Jan. 1991.*
Glukhov et al. Molekuliarnaia Biologiia 24(3): 781–787, Abstract only, May 1990.*
Carl T. Wittwer, and D. J. Garling, BioTechniques; Jan. 1991, vol. 10, No. 1 pp 76–78 and 80–83.
Maniatis et al., Molecular Cloning: A Laboratory Manual, pp. 280–281, (1982).
The Molecular Basis of Cell Structure and Function, $2^{nd}$ Edition, Lehninger, Worth Publishers, Inc. 1970, pp. 876–877.
Wittwer et al. (Anal. Biochem, 186 (2), pp 328–331, May 1, 1990.
Guatelli et al., Clin. Microbiol. Rev., 2(2), pp. 217–226 (1989).
Laure et al in The Lancet, pp. 538–540 (Sep. 3, 1988).
Cross–Belland et al. in Eur. J. Biochem, 36, 32 (1973).
Bell et al, Proc. Natl. Acad. Sci. USA, 78(9), pp. 5759–5763 (1981).
Saiki et al., Bio/Technology, 3, pp 1008–1012 (1985).
Hoffman et al, Biotechniques, 6(10), pp. 932–936 (1988).
Innis et al (Eds.), PCR Protocols: A Guide to Methods and Applicants, Chapter 51, pp. 429–434 by Robert Watson, Academic Press, Inc. 1990.
Agrawal et al. Nucleic Acids Res., 14, pp. 6227–6245 (1986).
Doetschman et al., Targeted Mutation of the Hprt Gene in Mouse Embryonic Stem Cells Proc. Natl. Acad. Sci. USA, vol. 85, p. 8583–8587, Nov. 1988.
Saiki: PCR Technology (H.A. Ehrlich ed.), p. 7–16, 1989.
Arrigo et al., Journl. Virol., 63, 4875–81, 1989.
Gelfand et al., PCR Protocols—A guide to methods and applications (Innis et al., Eds.) Chapter 16, 1990.
Ross et al., PNAS, 46, 1360–65, 1960.
Bonner et al., J. Mol. Biol., 81, 123–35, 1973.
Gelfand et al., PCR Protocols–A guide to methods and applications (Innis et al., Eds.) Chapter 16, 1990.
Kim et al., NAR, 16, 8887–8903, 1988.

* cited by examiner

Primary Examiner—Lisa B. Arthur
(74) Attorney, Agent, or Firm—Catherine K. Gowen

(57) ABSTRACT

Nucleic acids can be amplified and detected using a very rapid polymerase chain reaction procedure. This procedure includes a series of steps which have critically defined temperature and time parameters. Each polymerase chain reaction cycle requires generally less than about two minutes, and in most cases less than 90 seconds. At least 5 units/100 $\mu$l of solution of thermostable DNA polymerase are used, and other preferred levels of primer concentrations facilitate the quick cycling in the amplification. In preferred embodiments, only two temperatures are used in the amplification.

29 Claims, No Drawings

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
         (A) LENGTH: 28 nucleotides
         (B) TYPE: Nucleic acid
         (C) STRANDEDNESS: Single
         (D) TOPOLOGY: Linear (ii) MOLECULE TYPE: Oligonucleotide primer (iii) HYPOTHETICAL: No (iv) ANTI-SENSE: No (vi) ORIGINAL SOURCE:

(vii) IMMEDIATE SOURCE:

(x) PUBLICATION INFORMATION:

(xi) SEQUENCE DESCRIPTION: SEQ ID NO: 1:

TTTGGTCCTT GTCTTATGTC CAGAATGC                                            28

(2) INFORMATION FOR SEQ ID NO: 2:

(i) SEQUENCE CHARACTERISTICS:
         (A) LENGTH: 28 nucleotides
         (B) TYPE: Nucleic acid
         (C) STRANDEDNESS: Single
         (D) TOPOLOGY: Linear (ii) MOLECULE TYPE: Oligonucleotide primer (iii) HYPOTHETICAL: No (iv) ANTI-SENSE: No (vi) ORIGINAL SOURCE:

(vii) IMMEDIATE SOURCE:

(x) PUBLICATION INFORMATION:

(xi) SEQUENCE DESCRIPTION: SEQ ID NO: 2:

ATAATCCACC TATCCCAGTA GGAGAAAT                                            28

(2) INFORMATION FOR SEQ ID NO: 3:

(i) SEQUENCE CHARACTERISTICS:
         (A) LENGTH: 20 nucleotides
         (B) TYPE: Nucleic acid
         (C) STRANDEDNESS: Single
         (D) TOPOLOGY: Linear (ii) MOLECULE TYPE: Oligonucleotide primer (iii) HYPOTHETICAL: No (iv) ANTI-SENSE: No (vi) ORIGINAL SOURCE:

(vii) IMMEDIATE SOURCE:

(x) PUBLICATION INFORMATION:

(xi) SEQUENCE DESCRIPTION: SEQ ID NO: 3:

```
CAACTTCATC CACGTTCACC                                                    20

(2) INFORMATION FOR SEQ ID NO: 4:

(i) SEQUENCE CHARACTERISTICS:
        (A) LENGTH: 20 nucleotides
        (B) TYPE: Nucleic acid
        (C) STRANDEDNESS: Single
        (D) TOPOLOGY: Linear (ii) MOLECULE TYPE: Oligonucleotide primer (iii) HYPOTHETICAL: No (iv) ANTI-SENSE: No (vi) ORIGINAL SOURCE:

(vii) IMMEDIATE SOURCE:

(x) PUBLICATION INFORMATION:

(xi) SEQUENCE DESCRIPTION: SEQ ID NO: 4:

ACACAACTGT GTTCACTAGC                                                    20

(2) INFORMATION FOR SEQ ID NO: 5:

(i) SEQUENCE CHARACTERISTICS:
        (A) LENGTH: 41 nucleotides
        (B) TYPE: Nucleic acid
        (C) STRANDEDNESS: Single
        (D) TOPOLOGY: Linear (ii) MOLECULE TYPE: Oligonucleotide probe gag region (iii) HYPOTHETICAL: No (iv) ANTI-SENSE: No (vi) ORIGINAL SOURCE:

(vii) IMMEDIATE SOURCE:

(x) PUBLICATION INFORMATION:

(xi) SEQUENCE DESCRIPTION: SEQ ID NO: 5:

ATCCTGGAAT TAAATAAAAT AGTAAGAATG TATAGCCCTA C                             41

(2) INFORMATION FOR SEQ ID NO: 6:

(i) SEQUENCE CHARACTERISTICS:
        (A) LENGTH: 31 nucleotides
        (B) TYPE: Nucleic acid
        (C) STRANDEDNESS: Single
        (D) TOPOLOGY: Linear (ii) MOLECULE TYPE: Oligonucleotide probe b-globin DNA (iii) HYPOTHETICAL: No (iv) ANTI-SENSE: No (vi) ORIGINAL SOURCE:

(vii) IMMEDIATE SOURCE:

(x) PUBLICATION INFORMATION:

(xi) SEQUENCE DESCRIPTION: SEQ ID NO: 6:

CCTCAAACAG ACACCATGGT GCACCTGACT C                                       31
```

NUCLEIC ACID AMPLIFICATION AND DETECTION METHODS USING RAPID POLYMERASE CHAIN REACTION CYCLE

This is a Continuation of prior application Ser. No.: 07/693,574, filed Apr. 30, 1991, now abandoned.

FIELD OF THE INVENTION

This invention relates to very rapid amplification and detection methods to detect nucleic acids using polymerase chain reaction.

BACKGROUND OF THE INVENTION

Nucleic acid probe technology has developed rapidly in recent years as researchers have discovered its value for detection of various diseases, organisms or genetic features which are present in small quantities in a human or animal test sample. The use of probes is based upon the concept of complementarity. DNA has two strands bound together by hydrogen bonds between complementary nucleotides (which are also known as nucleotide pairs).

The DNA complex is normally stable, but the strands can be separated (or denatured) by conditions which disrupt the hydrogen bonding. The released single strands will reassociate only with another strand having a complementary sequence of nucleotides. This hybridization process can occur with both strands being in solution or with one of the strands being attached to a solid substrate.

A targeted nucleic acid sequence in an organism or cell may be only a very small portion of the entire DNA molecule so that it is very difficult to detect its presence using most labeled DNA probes. Much research has been carried out to find ways to detect only a few molecules of a targeted nucleic acid.

A significant advance in the art is described in U.S. Pat. No. 4,683,195 (issued Jul. 28, 1987 to Mullis et al), U.S. Pat. No. 4,683,202 (issued Jul. 28, 1987 to Mullis) and U.S. Pat. No. 4,965,188 (issued Oct. 23, 1990 to Mullis et al). Without going into extensive detail, these patents describe amplification and detection methods wherein primers are hybridized to the strands of a targeted nucleic acid (considered the templates) in the presence of a nucleotide polymerization agent (such as a DNA polymerase) and deoxyribonucleoside triphosphates. Under specified conditions, the result is the formation of primer extension products as nucleotides are added along the templates from the 3'-end of the primers. These products are then denatured and used as templates for more of the same primers in another extension reaction. When this cycle of denaturation, hybridization and primer extension is carried out a number of times (for example 25 to 30 cycles), the process which is known as "polymerase chain reaction" exponentially increases the original amount of targeted nucleic acid so that it is readily detected.

Once the targeted nucleic acid has been sufficiently amplified (that is, many times more copies of the molecule have been made), various detection procedures can be used to detect it. The patents noted above, for example, describe the use of insolubilized or detectably labeled probes and gel electrophoresis as representative detection methods.

In U.S. Pat. No. 4,965,188 (noted above), the cycle for amplification is generally described as follows:

a) denaturation at a temperature in the range of 90 to 105° C. (preferably 90 to 100° C.) for 0.5 to 5 minutes (preferably 0.5 to 3 minutes), b) hybridization of primer to template at a temperature in the range of 35 to 65° C. (preferably 37 to 60° C.) for 0.5 to 5 minutes (preferably 1 to 3 minutes), and c) formation of primer extension products at a temperature in the range of 40 to 80° (preferably 50 to 75° C.) for 0.5 to 40 minutes (preferably 1 to 3 minutes.

Thus, a wide range of times and temperatures are generally described with the specific combination of time and temperature largely dependent upon the type of DNA polymerase used, the complexity of the mixture of nucleic acids including the targeted nucleic acid, the length and specificity of the primers, the length of the targeted nucleic acid, pH and several other reaction conditions and components. There is no mention, however, of the time needed to change from one temperature to another, a factor which is largely dependent upon the type of heat transfer equipment used in the process. Thus, considerable effort must be carried out to find the optimum conditions for effective amplification and detection of a given nucleic acid.

One typical amplification cycle in Example II of U.S. Pat. No. 4,965,188 (noted above) requires about 5.5 minutes for a single cycle of the following steps:

a) heating the reaction mixture from 37 to 95° C. over three minutes, b) denaturation of double strands at 95° C. for 0.5 minutes, c) cooling to 37° C. over 1 minute, and d) hybridization of primers to template and primer extension product formation at 37° C. for 1 minute.

Another typical amplification cycle is described in Example VII of U.S. Pat. No. 4,965,188, also requires 5.5 minutes and includes the steps:

a) heating the reaction mixture from 70 to 98° C. over 1 minute, b) denaturing of double strands at 98° C. for 1 minute, c) cooling to either 38, 45 or 55° C. over 1 minute, d) hybridizing primers and template at 38, 45 or 55° C. for 1 minute, e) heating from 38, 45 or 55° C. to 70° C. over 1 minute, and f) forming primer extension products at 70° C. for 0.5 minute.

Since the discovery of the amplification and detection methods using polymerase chain reaction, there has been steady effort to find ways to carry out cycling in a rapid manner. A number of publications have suggested the desirability of fast cycling, but have not given suitable directions as to how it can be done. For example, rapid cycling is somewhat dependent upon suitable instrumentation. Details of such instrumentation are provided, for example, in EP-A-0 236 069 (published Sep. 9, 1987 and corresponding to U.S. Ser. No. 833,368 filed Feb. 25, 1986 and U.S. Ser. No. 899,061 filed Aug. 22, 1986). Cetus Corporation and Perkin-Elmer have developed commercially available thermocycling equipment which have enabled the user to perform a polymerase chain reaction cycle in from 3 to 6 minutes, similarly to the examples shown in U.S. Pat. No. 4,965,188 (noted above). While it may seem that a 3 to 6 minute cycle is quite fast, if one considers that efficient amplification generally requires 25 to 30 cycles to render the nucleic acid detectable, a typical standard amplification method could require 75 to 180 minutes.

More recently, Cetus Corporation and Perkin-Elmer have marketed a thermocycler (PCR System Model 9600) which allows the use of cycles of about 2 to 3 minutes in the amplification procedure.

Others have worked to find even faster cycling equipment which can be used with self-contained reaction vessels (sometimes known as cuvettes, pouches or test packs). Such equipment is described, for example in U.S. Ser. Nos. 452,666 and 452,932 (both filed Dec. 18, 1989 by Devaney Jr. et al), both as CIPs of U.S. Ser. No. 365,079 (filed Jun. 12, 1989). A typical reaction vessel useful with such equipment is described in U.S. Ser. No. 339,923 (filed Apr. 17, 1989 by Schnipelsky et al) as a CIP of U.S. Ser. No. 306,735 (filed Feb. 3, 1989).

It has been recognized that efficient heat transfer in the cycling of reaction mixtures will aid in the reduction of time required for a polymerase chain reaction cycle. For example, Wittwer et al (*Anal. Biochem.*, 186 (2), pp. 328–331, May 1, 1990) describe the use of hot air for heat transfer with reaction mixtures. Cycles lasting 30, 60, 120 and 180 seconds are described with the following steps in each cycle (as described for the 30 second cycle with longer cycles having proportionately longer steps):

a) denaturation of double strands at 90–92° C. for 1 to 2 seconds, b) cooling to 50 to 55° C. over 6 to 9 seconds, c) hybridization at 50 to 55° C. for 1 to 2 seconds, d) heating to 71 to 73° C. over 3 to 5 seconds, and e) forming primer extension products for 5 to 10 seconds.

The advantages of hot air heat transfer are described by Wittwer et al, and it is speculated that amplification can occur in minutes depending upon the reaction vessel and heat transfer equipment. The particular equipment described by Wittwer et al has a number of practical disadvantages, however, including the difficulty in loading samples and reagents into very small diameter capillary tubes, the fragility of those tubes (suitable for laboratory environment only, and not in high volume clinical environment), sealing the tubes with a flame (not practical in clinical setting) and the danger of contamination and contagion in removing the products of amplification from the tubes. In addition, it is not easy to control the heat transfer when air is the transfer means. In summary, such procedures may be readily adaptable to low volume research situations, but would not be practical or commercializable for high volume clinical settings or doctors' offices.

There is a continuing need in the art for a rapid and efficient amplification process which maintains the high amplification efficiency of the longer cycle times, but which greatly reduces the time for obtaining an analytical result. It is also desired to avoid the disadvantages noted above for standard methods using hot air transfer technology. Moreover, it is desired to have a rapid and sensitive amplification and detection process which is not dependent upon the particular type of heat transfer equipment that is used.

SUMMARY OF THE INVENTION

The problems noted with known methods are overcome with a method for the amplification of a nucleic acid comprising the steps of:

A. heating a targeted double-stranded nucleic acid at a first temperature of from about 85 to about 100° C. for from about 1 to about 40 seconds to denature the strands of the nucleic acid, B. cooling the denatured strands to a second temperature over a time period of from about 5 to about 20 seconds, C. in the presence of
1) a thermostable DNA polymerase present in an amount of at least 5 units/100 $\mu$l of solution,
2) deoxyribonucleotide-5'-triphosphates present in amounts effective for DNA polymerization, and
3) a set of primers specific for the denatured strands, said primers being present in amounts effective for DNA polymerization, forming hybridized primer extension products of the primers and denatured strands by incubating the denatured strands at a third temperature for from about 1 to about 80 seconds, the third temperature being in the range of from about $(T_m-15)°$ C. to about $(T_m+5)°$ C. wherein $T_m$ is the melting temperature of the denatured strands and the primers, and the difference ($\Delta T$) between the first and third temperatures being from about 5 to about 35° C., D. heating the hybridized primer extension products to the first temperature over a period of time of from about 5 to about 20 seconds and keeping the products at that temperature for from about 1 to about 40 seconds, and E. repeating steps B through D sequentially as a cycle at least once wherein each cycle of steps B through D is carried out within up to about 120 seconds, steps A through E further being carried out using at least one of the conditions selected from the group consisting of:

(a) the difference ($\Delta T_1$) between the first and second temperatures being from about 5 to about 45° C., and (b) the concentration of each of the primers being at least about 0.075 $\mu$molar, provided that when steps A through E are carried out using only condition (a), the time for each cycle of Steps B through D is at least about 60 seconds.

The present invention also provides a method for the amplification and detection of a nucleic acid comprising steps A-E and the conditions as identified above taken in addition with the following step F:

F. detecting at least one denatured strand of the nucleic acid.

The method of this invention provides a very rapid and efficient polymerase chain reaction procedure for amplifying and detecting nucleic acids which are present in extremely low concentrations in test samples. Because the method is rapid, an assay result can be obtained in shorter time for early diagnosis, or more cycles can be run in order to further increase the number of copies of the targeted nucleic acid. With shorter cycles, less nonspecific (or undesired) nucleic acids are amplified. Thus, less of the undesired nucleic acids are detected.

The method of this invention is advantageous because it is readily adaptable to automated procedures which can be used in high volume diagnostic environments (for example, hospitals, clinical laboratories and doctors' offices). The impractical features of the hot air PCR procedures of Wittwer et al are avoided. Each cycle of the PCR method of this invention is extremely rapid (that is 120 seconds or less), yet it is not dependent upon a particular means of heat transfer or specific heat transfer equipment.

These advantages are possible because of a combination of critical features, namely the use of relatively high concentrations of the thermostable DNA polymerase, a temperature for DNA polymerization which is related to the $T_m$ of the denatured strands and the primers with one or both of two other conditions: (a) having the difference between the denaturation and hybridization temperatures being within a certain range, or (b) having the concentration of primers at or above about 0.075 $\mu$molar, with the proviso that if only condition (a) is used, the cycle time is at least about 60 seconds. In preferred embodiments, the method is even faster by using only two temperatures in the cycling instead of the usual three temperatures.

Advantageously, this invention is carried out using certain proprietary containment pouches and cycling equipment, namely those described in U.S. Ser. Nos. 339,923, 452,666 and 452,932 (all noted above), but the practice of this invention is not limited to them.

DETAILED DESCRIPTION OF THE INVENTION

The general principles and conditions for amplification and detection of nucleic acids using polymerase chain reaction are quite well known, the details of which are provided in numerous references including U.S. Pat. Nos. 4,683,195, 4,683,202 and 4,965,188 (noted above) and by Guatelli et al, Clin. Microbiol. Rev., 2(2), pp. 217–226 (1989). Thus, many of the details of such technology are not included herein. However, in view of the teaching in the art and the specific teaching provided herein, a worker skilled in the art should have no difficulty in practicing the present invention by making the adjustments taught herein to accomplish more rapid amplification.

The present invention is directed to the amplification or detection of one or more specific nucleic acid sequences present in one or more targeted nucleic acids in a test specimen. Such specimens can include cellular or viral material, hair, body fluids or other materials containing genetic DNA or RNA which can be detected. While the primary purpose of detection is diagnostic in nature, the invention can also be used to improve the efficiency of cloning DNA or messenger RNA, or for obtaining large amounts of the desired sequence from a mixture of nucleic acids resulting from chemical synthesis.

The present invention is especially useful for producing, in exponential quantities relative to the number of reaction steps involved, at least one specific nucleic acid sequence. The product will be a discrete nucleic acid duplex with termini corresponding to the ends of the specific primers employed. Any source of nucleic acid, purified or not, can be utilized as the starting material if it is known to or suspected of containing the specific nucleic acid sequence targeted for detection. A mixture of nucleic acids can be employed if desired. The sequence to be duplicated can be a fragment of the entire nucleic acid. Moreover, a plurality of double stranded nucleic acids can be amplified and detected simultaneously by using a corresponding set of primers and detection means for each specific nucleic acid. Multiple sequences in the same nucleic acid can also be amplified and detected.

Nucleic acids to be detected can be obtained from various sources including plasmids, naturally occurring DNA or RNA from any source (such as bacteria, yeast, viruses, plants and higher animals, humans). It may be extracted from various tissues including blood, peripheral blood mononuclear cells (PBMC), tissue material or other sources known in the art using known procedures. The present invention is particularly useful for the amplification and detection of nucleic acid sequences found in genomic DNA, bacterial DNA, fungal DNA, viral RNA, or DNA or RNA found in bacterial or viral infected cells.

The method described herein can be used to provide the detection or characterization of specific nucleic acid sequences associated with infectious diseases, genetic disorders or cellular disorders such as cancers. It may also be used in forensic investigations and DNA typing. For purposes of this invention, genetic diseases include specific deletions or mutations in genomic DNA from any organism, such as sickle cell anemia, cystic fibrosis, α-thalessemia, β-thalessemia and others readily apparent to one skilled in the art. Human Leukocyte Antigen (HLA) can be categorized with the present invention. Various infectious diseases can be diagnosed by the presence in a clinical sample of small quantities of specific DNA sequences characteristic of the organism, whether it be a yeast, bacterium or virus. Such bacteria which can be detected include, but are not limited to, Salmonella, Streptococcal organisms, Chlamydial organisms, Gonococcal organisms, *Mycobacterium tuberculosis*, *Mycobacterium avium* complex, *Mycoplasma Haemophilus influenzae*, Shigella and Listeria. Viruses which are detectable include, but are not limited to, herpes, Epstein Barr virus, cytomegalovirus, human papilloma virus, hepatitis and retroviruses such as HTLV-I, HIV-I and HIV-II. Protozoan parasites, yeasts and molds are also detectable. Other detectable species would be readily apparent to one skilled in the art. The invention is particularly useful for the detection of the presence of DNA associated with various bacteria or viruses, with the amplification and detection of viral DNA being of most interest. Detection of DNA associated with HIV-I (and other retroviruses), cytomegalovirus or human papilloma virus is advantageously accomplished with this invention. Most preferably, it is used to detect DNA associated with retroviruses, such as HIV-I.

As used herein in referring to primers, probes or oligomer fragments to be detected, the term "oligonucleotide" refers to a molecule comprised of two or more deoxyribonucleotides or ribonucleotides, and preferably more than three. Its exact size is not critical but depends upon many factors including the ultimate use or function of the oligonucleotide. The oligonucleotide may be derived synthetically, by cloning or by other methods known in the art.

The term "primer" refers to an oligonucleotide, whether naturally occurring or synthetically produced, which is capable of acting as a point of initiation of synthesis when placed under conditions in which synthesis of a primer extension product complementary to a nucleic acid strand (that is, template) is induced. Such conditions include the presence of nucleotides (such as the four standard deoxyribonucleoside-5'-triphosphates) and an agent for polymerization such as a DNA polymerase, and suitable temperature, pH and cofactors.

The primer is preferably single stranded for maximum efficiency in amplification, but contain a double stranded region if desired. Preferably, the primer is an oligodeoxyribonucleotide. It must be long enough to prime the synthesis of extension products in the presence of the DNA polymerase. The exact size of each primer will vary depending upon the use contemplated, the complexity of the targeted sequence, reaction temperature and the source of the primer. Generally, the primers used in this invention will have from 12 to 60 nucleotides, and preferably, they have from 18 to 45 nucleotides.

In the practice of this invention, any of the primers used can contain a double-stranded, labeled nucleic acid region adjacent to a single-stranded region. The single-stranded region contains a nucleic acid sequence which is sufficiently complementary to the template strand to hybridize therewith. The double-stranded region, or tail, of the primer can be labeled with a detectable moiety which is capable of producing a detectable signal or which is useful in capturing or immobilizing the extension product. Further details regarding such primers, useful labels, and methods of preparation are available in U.S. Ser. No. 076,394 (filed Jul. 22, 1987 by Watson et al).

The primers used in the present invention are selected to be "substantially complementary" to the different strands of each specific sequence to be amplified. This means that they must be sufficiently complementary to hybridize with their respective strands to form the desired hybridized products and then be extendable by a DNA polymerase. In the preferred and most practical situation, the primer has exact complementarity to the target nucleic acid. However, in many situations, exact complementarity is not possible or likely, and one or more mismatches may exist which do prevent hybridization or the formation of primer extension products using the DNA polymerase.

In some situations where mismatches between the targeted nucleic acid and a primer are suspected, the effect of the mismatch may be overcome using specialized primer compositions, such as those described for example in EP-A-0 393 743 (published Oct. 24, 1990) and U.S. Ser. No. 406,221 (filed Sep. 12, 1989 by Findlay, corresponding to EP-A-0 417 842, published Mar. 20, 1991).

Primers useful herein can be obtained from a number of sources or prepared using known techniques and equipment, including for example, an ABI DNA Synthesizer (available from Applied Biosystems) or a Biosearch 8600 Series or 8800 Series Synthesizer (available from Milligen-Biosearch, Inc.) and known methods for their use (for example as described in U.S. Pat. No. 4,965,188, noted above). Naturally occurring primers isolated from biological sources are also useful (such as restriction endonuclease digests). As used herein, the term "primer" also refers to a mixture of primers such as may be used to detect targeted nucleic acids which may vary from specimen to specimen, or which may be used to overcome suspected mismatches between a primary primer and the template.

As used herein, a "probe" is an oligonucleotide which is substantially complementary to a nucleic acid sequence of the targeted nucleic acid and which is generally not able to form primer extension products. The probes can be of any suitable length of nucleotides, but generally, they have from about 12 to about 40 nucleotides. They are labeled (commonly at the 3' end) with any suitable detectable material (either directly or indirectly), as described below. They can also be attached to a water-insoluble substrate of some type for capture of the targeted nucleic acid.

A "thermostable DNA polymerase", as is known in the art, is an enzyme which will function to accomplish the synthesis of primer extension products, and which is stable to heat, especially the high temperatures used for denaturation of DNA strands. More particularly, the thermostable DNA polymerases must not be substantially inactivated at the high temperatures used in polymerase chain reactions as described herein. Such temperatures will vary depending upon a number of reaction conditions, including pH, the nucleotide composition of the targeted nucleic acid and primers, the length of primer, salt concentration and other conditions known in the art and will be in the ranges noted below.

A number of thermostable DNA polymerases have been reported in the art, including those mentioned in detail in U.S. Pat. No. 4,965,188 (noted above) and U.S. Pat. No. 4,889,818 (issued Dec. 26, 1989 to Gelfand et al). Particularly useful polymerases are those obtained from various Thermus bacterial species, such as *Thermus aquaticus*, *Thermus thermophilus* or *Thermus flavus*. Other useful thermostable polymerases are described in WO-A-89/06691 (published Jul. 27, 1989). Some useful polymerases are commercially available. A number of techniques are known for isolating naturally-occurring polymerases from organisms, and for producing genetically engineered enzymes using recombinant techniques, as noted in the art cited in this paragraph.

Synthesis of extension products is initiated at the 3' end of each primer and proceeds in the 5' to 3' direction of the newly synthesized strand (or in the 3' to 5' direction of the template) until synthesis is terminated.

A targeted nucleic acid (that is, one to be amplified or detected) can be obtained from any of a variety of sources as noted above. Generally, it is extracted in some manner to make it available for contact with the primers and other reaction materials. This usually means removing unwanted proteins and cellular matter from the specimen in a suitable manner. Various procedures are known in the art, including those described by Laure et al in *The Lancet*, pp. 538–540 (Sep. 3, 1988), Maniatis et al, *Molecular Cloning: A Laboratory Manual*, pp. 280–281 (1982), Gross-Belland et al in *Eur. J. Biochem.*, 36, 32 (1973) and U.S. Pat. No. 4,965,188 (noted above). Extraction of DNA from whole blood or components thereof are described, for example, in EP-A-0 393 744 (published Oct. 24, 1990), Bell et al, *Proc. Natl. Acad. Sci. USA*, 78(9), pp. 5759–5763 (1981) and Saiki et al, *Bio/Technology*, 3, pp. 1008–1012 (1985).

Since the nucleic acid to be amplified or detected is usually in double stranded form, the two strands must be separated (that is, denatured before priming can take place). This can occur during the extraction process, or be a separate step afterwards. Denaturing (step A) is accomplished using a heat treatment alone or in combination with any suitable other physical, chemical or enzymatic means as described in the art. Heating alone to a suitable temperature is a preferred means. Initial denaturation is generally carried out by heating the specimen suspected of containing the targeted nucleic acid at a first temperature of from about 85 to about 100° C. for from about 1 to about 40 seconds. Preferably, this denaturation requires only from about 1 to about 20 seconds at from about 90 to about 98° C. but other combinations of time and temperature within the broad ranges would be readily determinable by one skilled in the art.

The denatured strands are then cooled (step B) to a second temperature which is generally in the range of from about 55 to about 70° C., and preferably from about 60 to about 70° C. A preferred condition of this invention is to adjust the first and second temperatures so that the difference between them (identified herein as $\Delta T_1$) is in the range of from about 5 to about 45, preferably from about 15 to about 45, and most preferably from about 25 to about 40° C. This condition is particularly desirable when the second and third (defined below) temperatures are the same. The time needed for cooling the denatured strands is generally from about 5 to about 20 seconds, and preferably from about 5 to about 15 seconds.

Once the denatured strands are cooled to the second temperature, step C is carried out. It should be understood, however, that there may not be a distinct time when step B ends and step C begins, but one skilled in the art would know how to adjust the individual steps to obtain rapid cycling as taught herein. In the presence of the DNA polymerization reagents identified below, hybridized primer extension products of the primers and denatured strands are formed by incubation at a third temperature for from about 1 to about 80 seconds, and preferably for from about 1 to about 40 seconds.

This third temperature is generally in the range of from about $(T_m-15)°$ C. to about $(T_m+5)°$ C. $T_m$ is defined herein as the temperature at which about one-half of the target nucleic acid strands will be hybridized to the primers. The determination of $T_m$ can be accomplished using several standard procedures, based on ultraviolet hypochromism, for example, by monitoring the spectrum at 260 nm as described in *Biochemistry—The Molecular Basis of Cell Structure and Function,* 2nd Edition, Lehninger, Worth Publishers, Inc., 1970, pp. 876–7.

In most embodiments, the third temperature is in the range of from about 55 to about 70° C. with from about 62 to about 68° C. being preferred. It is also desired that the difference between the first and third temperatures (identified herein as $\Delta T$) be in the range of from about 5 to about 35, preferably from about 10 to about 35, and most preferably from about 20 to about 30° C. In a preferred embodiment where the cycling is carried out using only two different temperatures, the second temperature is the same as the third temperature, and thus $\Delta T_1$ is the same as $\Delta T$.

Once the strands are separated, they are available as templates for forming primer extension products therewith. Normally, the specimen is mixed with the thermostable DNA polymerase, suitable deoxyribonucleotide-5'-triphosphates (dATP, dCTP, dGTP and dTTP) and a suitable set of primers. The amount of thermostable DNA polymerase used in the practice of this invention is at least about 5 units/100 $\mu$l of solution. Preferably the amount is in the range of from about 6 to about 20 units/100 $\mu$l of solution but greater amounts can be used if desired. A "unit" is defined herein as the amount of enzyme activity required to incorporate 10 nmoles of total nucleotides (dNTP's) into an extending nucleic acid chain in 30 minutes at 74° C.

The dNTP's and primers are present in amounts effective for DNA polymerization to occur, such amounts being known in the art. Representative amounts are shown in the examples below. In a preferred embodiment, the amount of primer is at least about 0.075 $\mu$molar with 0.1 to 2 $\mu$molar being preferred, but more general amounts are well known in the art. Another measure for the primers is to have them in considerable excess to the denatured strands, for example at least about 20:1 molar ratio. It is understood that where the amount of targeted nucleic acid is unknown, the exact ratio of primer to denatured strand cannot be known with certainty, but a skilled worker could make a reasonable estimate of the amount of primer to be used and thus optimize the reaction system accordingly in view of the considerable teaching in the art regarding reagent amounts.

Other reagents are also preferably present, including salts such as magnesium chloride (generally from about 1 to about 10 mmolar), extenders such as gelatin or other water soluble or water dispersible colloids (generally from about 0.001 to about 0.05 weight percent). The reaction mixture is generally buffered to a pH of from about 7 to about 9 with pH of about 8 being preferred using any of a number of suitable buffers known in the art. The volume of the reaction mixture including the targeted nucleic acid is not critical, but the smaller the volume is the faster heat can be transferred to and away from it. Generally, the volume is from about 50 to about 300 $\mu$l with smaller or larger volumes also being useful depending upon the equipment and vessel used for the assay.

The reagents for polymerization can be added to the specimen containing targeted nucleic acid at any suitable time, that is, prior to or during denaturation (Step A or D), or prior to, during or after the cooling step (Step B). Alternatively, the reagents can be added at several and various times during the method. Workers skilled in the art would be able to design an acceptable protocol for reagent addition. It is important for the mixing to take place quickly so the method is carried out in the shortest possible time. Thus, it is preferred that all the reagents needed for the entire method be added prior to or during the denaturation Step A of the method defined herein.

The newly synthesized hybridized product of the template and its complementary nucleic acid formed from the primer are used in subsequent steps of the method. They are then denatured by heating them to the first temperature of from about 85 to about 100° C. over a period of time of from about 5 to about 20 seconds, and maintaining that temperature for an additional time of from about 1 to about 40 seconds (step D). Preferably, the denaturation temperature is from about 90 to about 98° C., the heating time is from about 5 to about 10 seconds, and the temperature is maintained for an additional 1 to about 15 seconds.

At this point, one cycle of forming and separating one set of duplicate strands of the targeted nucleic acid has been completed (steps B through D). Each cycle is about 120 seconds or less, and is generally in the range of from about 10 seconds to about 120 seconds. Preferably, each cycle is from about 20 to about 90 seconds, with from about 30 to about 70 seconds being more preferred. The cycle can be completed as often as needed to produce the desired quantity of the targeted nucleic acid. The only limitation is the amount of DNA polymerase, primers and triphosphates used.

The cycle is repeated at least once (step E). For effective amplification, at least 20 cycles of cooling, primer extension and denaturation will be carried, with from 20 to 40 cycles being preferred.

The method of amplifying described herein is also carried out using at least one (and preferably both) of the conditions selected from the group consisting of:

(a) $\Delta T_1$, identified above, is from about 5 to about 45° C., and (b) the concentration of each primer is at least about 0.075 $\mu$molar.

If only condition (a) is used, the time for each cycle of Steps B through D is at least about 60 seconds, and preferably, each cycle is from about 90 to about 120 seconds.

In a most preferred embodiment, both of these conditions are followed and the second temperature is the same as the third temperature.

After step C has been performed the last time in the assay, the final primer extension products can be detected using known procedures, as described below. The products can be detected in undenatured form using known procedures such as agarose gel electrophoresis or ethidium bromide staining, or step D can be performed again to denature the products for detection.

Preferably, the products are denatured a last time (step D) providing multiple copies of the strands of the targeted nucleic acid. Denaturation can be carried out according to the teaching noted above except that the time for denaturation the last time is not as critical as it is in earlier cycles (that is, it can be longer if desired).

After the desired number of cycles, the reaction can also be stopped by inactivating the DNA polymerase using known techniques, or by separating the components of the reaction.

The amplification method of this invention is preferably conducted in a continuous, automated manner so that the reaction mixture is temperature cycled in a controlled manner for desired preset times. A number of instruments have been developed for this purpose, as one of ordinary skill in the art would know.

One such instrument for this purpose is described in some detail in U.S. Pat. No. 4,965,188 (noted above) and EP-A-0 236 069 (noted above), and involves moving liquids from one temperature environment to another under controlled conditions.

Another instrument utilizes temperature cycling without a liquid handling system, and is described in some detail in U.S. Pat. No. 4,965,188and EP-A-0 236 069 (noted above). Generally, this instrument includes a heat conducting container for holding a number of reaction tubes containing reaction mixture, a means for heating, cooling and temperature maintenance, and a computing means to generate signals to control the amplification sequence, changes in temperature and timing.

A gas chromatograph has also been used for amplification, as described for example by Hoffman et al, *Biotechniques*, 6(10), pp. 932–936 (1988), and amplification in a "teacup" has been described as a simple and inexpensive, Innis et al (Eds.), *PCR Protocols: A Guide to Methods and Applicants*, Chapter 51, pp. 429–434 by Robert Watson, Academic Press, Inc., 1990.

A preferred instrument for processing amplification reactions in a disposable chemical test pack is described in some detail in U.S. Ser. No. 452,666 (filed Dec. 18, 1989 by Devaney Jr. et al as a CIP of U.S. Ser. No. 365,079, filed Jun. 12, 1989). In general, this instrument comprises a support surface for supporting a chemical test pack, pressure applicators supported above the surface for acting on the reaction pack to transfer fluids between adjacent chambers in the test pack, and means for operating the pressure applicators through a range of movement extending across the test pack.

U.S. Ser. No. 452,932 (filed Dec. 18, 1989 by Devaney Jr. et al as a CIP of U.S. Ser. No. 365,079 filed Jun. 12, 1989) provides details of useful chemical test packs which can be processed using the instrument described in U.S. Ser. No. 452,666 (noted above). Also described therein are means for heating and cooling the test pack at repeated intervals (that is, through cycles) appropriate for the method of the present invention. As noted above, while these instruments and test packs are preferred in practicing the present invention, they are not considered essential to obtaining the beneficial results noted herein.

The method of this invention can be used to advantage to rapidly detect or characterize a targeted nucleic acid which is present in an infectious agent. Detection can be accomplished in a number of known ways, such as those described in U.S. Pat. No. 4,965,188 (noted above). For example, the amplified nucleic acid can be analyzed using Southern blotting techniques. Alternatively, amplification can be carried out using radioisotopic or biotinylated primers which can then be detected using appropriate techniques. Sequence specific oligonucleotides can be used with dot blot techniques to detect single-base pair variations in nucleic acids.

In one preferred embodiment, once a desired amount of the nucleic acid sequence of interest has been generated and the primer extension products are denatured for a last time, the amplified targeted nucleic acid is detected using an oligonucleotide probe which is labeled for detection and can be directly or indirectly hybridized with one of the primer extension products. Procedures for attaching labels and preparing probes are well known in the art, for example, as described by Agrawal et al, *Nucleic Acid Res.*, 14, pp. 6227–45 (1986), U.S. Pat. No. 4,914,210 (issued Apr. 3, 1990 to Levenson et al) relating to biotin labels, U.S. Pat. No. 4,962,029 (issued Oct. 9, 1990 to Levenson et al) relating to enzyme labels, and the references noted therein. Useful labels include radioisotopes, electron-dense reagents, chromogens, fluorogens, phosphorescent moieties, ferritin and other magnetic particles (see U.S. Pat. No. 4,795,698 issued Jan. 3, 1989 to Owen et al and U.S. Pat. No. 4,920,061 issued Apr. 24, 1990 to Poynton et al), chemiluminescent moieties and enzymes (which are preferred). Useful enzymes include, glucose oxidase, peroxidases, uricase, alkaline phosphatase and others known in the art and can be attached to oligonucleotides using known procedures. Substrates and dye forming compositions for such enzymes are well known. The labeled primers described in U.S. Ser. No. 076,394 (noted above) can also be used as probes in the practice of this invention.

Where the label is a preferred enzyme such as a peroxidase, at some point in the assay, hydrogen peroxide and suitable dye-forming compositions are added to provide a detectable dye. For example, useful dye-providing reagents include tetramethylbenzidine and derivatives thereof, and leuco dyes, such as triarylimidazole leuco dyes (as described in U.S. Pat. No. 4,089,747 issued May 16, 1978 to Bruschi), or other compounds which react to provide a dye in the presence of peroxidase and hydrogen peroxide. Particularly useful dye-providing compositions are described in U.S. Ser. No. 136,166 (filed Dec. 18, 1987 by McClune et al corresponding to EP-A-0 308 236, published Mar. 22, 1989).

Detection of the presence of the probe which is in the complementary product can be achieved using suitable detection equipment and procedures which are well known. Certain probes may be visible to the eye without the use of detection equipment.

In an alternative embodiment, a primer is biotinylated and the amplified nucleic acid is detected using detectably labeled avidin or derivative thereof. For example, avidin can be conjugated with an enzyme, or have a radioactive moiety. Biotin on the amplified product complexes with the avidin, and appropriate detection techniques are used.

Other formats for detection are well known in the art which includes standard hybridization procedures (such as "sandwich assays), and other procedures described in the amplification art such as U.S. Pat. No. 4,965,188 (noted above).

It is also useful for the method of this invention to be carried out in a suitable container. The most crude container would be a test tube, cuvette, flask or beaker, but more sophisticated containers have been fashioned in order to facilitate automated procedures for performing the method. For example, a cuvette constructed to provide certain temperature characteristics during the practice of the method is described in U.S. Pat. No. 4,902,624 (issued Feb. 20, 1990 to Columbus et al), and U.S. Ser. No. 339,923, filed on Apr. 17, 1989 by Schnipelsky et al as a CIP of U.S. Ser. No. 306,735, filed Feb. 3, 1989). Such containers are also known as chemical test packs (or pouches) according to U.S. Ser. No. 452,932 (noted above). Such test packs have a multiplicity of reaction chambers having various reagents, buffers and other materials which are useful at various stages in the amplification method. The packs can be appropriately and rapidly heated and cooled in cycles to promote the various steps of the amplification method of this invention. Other useful containers could be suitably fashioned for automated or single use of the method of this invention.

In order for the amplified product to be detected, it is often useful (but not necessary) for it to be separated from the other materials in the reaction medium. This is done by any of a number of ways, including using a water-insoluble capture means on a primer or probe so that the primer extension products which are replicated in the method are water-insolubilized and removed from the reagent mixture. Primers or probes can be attached to insoluble materials in a suitable manner, or they can be designed to be capturable, that is, reactive with a capture means at some point in the method.

One useful capture means is described in EP-A-0 370 694 (published May 30, 1990). A primer has a specific binding ligand attached thereto (such as biotin, an antibody or a lectin) which is capable of specifically binding to a receptor molecule (such as avidin, an antigenic material or a sugar) which is bound in a suitable manner to an insoluble material such as polymeric particles. The resulting insolubilized specifically bound product can be separated from water-soluble materials by filtration, centrifugation or other suitable separation techniques. Detection of the captured nucleic acid strand can be accomplished directly using a probe complementary thereto, or indirectly using one or more intermediate oligonucleotides to which a labeled probe can be hybridized.

Alternatively, the amplified product can be separated from undesired materials by using an oligonucleotide complementary thereto, which oligonucleotide is attached to an insoluble substrate (such as polymeric particles) using known attachment techniques. One such technique is described in U.S. Ser. No. 471,168 (filed Jan. 26, 1990 by Warren III et al). Other techniques are described for example in U.S. Pat. No. 4,713,326 (issued Dec. 15, 1987 to Dattagupta et al), WO-A-88/01302 (published Feb. 25, 1988) and EP-B-0 070 687 (published Jan. 26, 1983) whereby intermediate oligonucleotides are used in a hybridized product of multiple components to which the capture oligonucleotide and amplified nucleic acid are joined.

Useful separation means are microporous filtration membranes such as the polyamide membranes marketed by Pall Corp. (for example as LOPRODYNE™ or BIODYNE™ membranes). They can be used uncoated or precoated with surfactants or other materials which facilitate the analytical procedures.

The membranes can be used as a separate substrate with suitable containers for carrying out other steps of the assay. Preferably, however, they are mounted as part of a test device. Various test devices are known in the art including those described in U.S. Pat. No. 3,825,410 (issued Jul. 23, 1974 to Bagshawe), U.S. Pat. No. 3,888,629 (issued Jun. 10, 1975 to Bagshawe), U.S. Pat. No. 3,970,429 (issued Jul. 20, 1976 to Updike) and U.S. Pat. No. 4,446,232 (issued May 1, 1984 to Liotta). Particularly useful devices are described in U.S. Pat. No. 4,921,677 (issued May 1, 1990) and are commercially available as SURECELL™ test devices and assay kits from Eastman Kodak Company.

Any useful solid support can be used for separation of water-insoluble product for detection, including a microtiter plate, test tube, beaker, beads, film, membrane filters, filter papers, gels, magnetic particles or glass wool. It can be made of a number of materials including glass, ceramics, metals, naturally occurring or synthetic polymers, cellulosic materials, filter materials and others readily apparent to one of ordinary skill in the art. Particularly useful solid support materials are polymeric beads generally having an average particle size of from about 0.1 to about 10 μmeters. Further details about such preferred polymeric particles, including useful monomers, methods of preparing them and attachment of receptor molecules, are provided in U.S. Ser. No. 136,165 (filed Dec. 18, 1987 by Sutton et al) and U.S. Ser. No. 539,774 (filed Jun. 18, 1990 by Sutton et al).

The detection can also be carried out by immobilizing a capture probe on a flat substrate, such as the microporous filtration membranes described above, or on thin polymeric films, uncoated papers or polymer coated papers, a number of which are known in the art. Other details about such materials are provided in U.S. Ser. No. 571,560 (filed Sep. 4, 1990 as a CIP of U.S. Ser. No. 306,954 (filed Feb. 3, 1989 by Findlay et al, and corresponding to EP-A-0 408 738, published Jan. 23, 1991).

The following examples are included to illustrate the practice of this invention, and are not meant to be limiting in any way. All percentages are by weight unless otherwise noted.

MATERIALS AND METHODS FOR EXAMPLES

A Perkin-Elmer Cetus thermocycler (Perkin-Elmer Corporation, labeled as "DNA Thermal Cycler") was used with the microfuge tube amplifications. Temperature profiles were checked using thermocoupled tubes. Mineral oil was put on top of the polymerase chain reaction mixture to prevent evaporation and condensation.

Chemical test pack amplifications were carried out using a dual-sided heater and processor as described in U.S. Ser. No. 452,666 (noted above). Thermocoupled chambers in chemical test packs were used to monitor the temperatures. These chambers were formed from a sheet of polyester (0.01 cm thickness) coated with polyethylene (SCOTCH PAK™ from 3M Co.), folded over to provide a circular chamber (sometimes called a "blister") about 1.3 cm in diameter. An opening was provided to permit the addition of the polymerase chain reaction mixture which was drawn into the chamber by vacuum. The opening was then heat sealed. After amplification, a corner of the chamber was cut, and the solution was transferred to a microfuge tube (0.5 ml) for storage at 4° C. until detection of the products was carried out.

The polymerase chain reaction mixture (100 ml) included tris(hydroxymethyl)aminomethane buffer (10 mmolar, pH 8), potassium chloride (50 mmolar), magnesium chloride (10 mmolar) dATP, dCTP, dGTP and dTTP (1.5 mmolar of each), primers (identified below, 1 μmolar of each), gelatin (0.01%), thermostable DNA polymerase (from *Thermus aquaticus*), recombinant form obtained from Cetus Corp. (75 units/100 ml).

The primers used for HIV-I DNA detection were as follows and were complementary to the gag region of the virus:

SEQ ID NO:1:

5'-X-TTTGGTCCTT GTCTTATGTC CAGAATGC-3' and

SEQ ID NO:2:

5'-ATAATCCACC TATCCCAGTA GGAGAAAT-3' wherein X represents biotin attached through an aminotetraethylene glycol spacer group using the procedures described in U.S. Pat. No. 4,962,029 (noted above).

The primers complementary to strands of β-globin DNA were:

SEQ ID NO:3:

5'-X-CAACTTCATC CACGTTCACC-3' and

SEQ ID NO:4:

5'-ACACAACTGT GTTCACTAGC-3' wherein X is as described above.

All primers and probes were prepared by standard phosphoramidite chemistry, purified by high pressure liquid chromatography and characterized by base composition analysis and electrophoresis high pressure liquid chromatography.

The capture probe for HIV-I DNA was as follows (SEQ ID NO:5):

5'-X-ATCCTGGAAT TAAATAAAAT AGTAAGAATG TATAGCCCTA C-3' wherein X is as defined above for the primers.

The capture probe for β-globin DNA was as follows (SEQ ID NO:6):

5'-X-CCTCAAACAG ACACCATGGT GCACCTGACT C-3' wherein X is as defined above.

The probes were attached to particles of poly(styrene-co-acrylic acid) (97.5:2.5 molar ratio, 1.3 μmeters average diameter). A suspension (1%) of the particles in glycine buffer (0.1 molar, pH 8.5) was washed twice with 2-(N-morpholino)ethanesulfonic acid buffer (0.1 molar, pH 6). A sample of the washed particles (30 mg) in buffer (1 ml) was mixed with 1-(3-dimethylaminopropyl)-3-ethylcarbodiimide hydrochloride (0.15 ml of 100 mg/ml buffer) and the appropriate probe (28.8 ml of 57.3 OD/ml nanopure water). The resulting mixture was rotated end-over-end at room temperature for 15 hours, centrifuged and the particles were washed three times with nanopure water and resuspended therein (1% solids).

HIV-I DNA target nucleic acid sequences were either M13/HIV (a 180 base pair segment of HIV-I cloned into M13 phage using standard procedures), or HUT 78 cell line DNA (a cell line which contains a single integrated copy of the HIV-I genome). These targeted sequences are prepared using standard DNA purification procedures.

The β-globin DNA target nucleic acid sequence was in human placental DNA (10 mg/ml) which is assumed to have two copies of the β-globin gene per cell.

The detection of the amplified nucleic acid was carried out by using either agarose gel electrophoresis (3% NUSIEVE™ agarose and 1% agarose from FMC Corporation), stained with ethidium bromide, or capture and detection in a SURECELL™ disposable test device (Eastman Kodak Company) and capture with the capture probe.

A salt buffer solution (250 ml) comprised sodium dihydrogen phosphate (10 mmolar, pH 7.4), sodium chloride (150 mmolar) and ethylenediaminetetraacetic acid (1 mmolar).

A leuco dye composition was prepared containing 2-(4-hydroxy-3,5-dimethoxyphenyl)-4,5-bis(4-methoxyphenyl) imidazole as follows: Solid leuco dye (to make a 0.1% solution) was dissolved in a solution of poly (vinylpyrrolidone) (20%) in sodium phosphate buffer (5 mmolar). This solution was then added to a solution of hydrogen peroxide (10 mmolar), 4'-hydroxyacetanilide electron transfer agent (5 mmolar) and diethylenetriaminepentaacetic acid chelating agent (10 mmolar) in sodium phosphate buffer to produce a final concentration of 1% polymer and 0.005% leuco dye.

A streptavidin-horseradish peroxidase conjugate was obtained from Zymed Labs (San Francisco), and diluted 1:8000 with a phosphate buffered saline solution containing casein (0.5%), 3-(N-morpholino)propanesulfonic acid buffer (100 mmolar, pH 7.5) and thimerosal preservative (0.01%). The final conjugate concentration was 156 ng/ml. The phosphate buffered saline solution contained sodium phosphate (25 mmolar, pH 7.3) and sodium chloride (75 mmolar).

Polymerase chain reaction was carried out in either microfuge tubes (100 ml) or in chemical test packs (180 ml) as noted above. The polymerase chain reaction solution containing the HIV-I DNA target (about $10^{-16}$ molar) and the appropriate primers was amplified for the noted cycles with noted temperature steps as indicated in the examples.

In the assays where the SURECELL™ disposable test devices are used, the probes on the polymeric particles (about 1 ml, 1% suspension) were deposited in defined regions of the microporous membranes (uncoated, 5 mm LOPRODYNE™ nylon from Pall Corp.) in the test devices and dried. A portion of the polymerase chain reaction solution (5 ml) was mixed with the buffer solution (95 ml) and incubated at 95° C. for 5 minutes to denature the nucleic acids. The solution was then transferred to the test devices to hybridize the amplified target nucleic acid to the immobilized probe on the membrane at 42° C. The test wells of the devices were washed with a solution (250 ml) comprising sodium decyl sulfate (1%) in the salt buffer solution at 55° C. A buffered solution containing the streptavidin conjugate (50 ml containing 7.8 ng of conjugate) was added at room temperature and allowed to flow through the membranes. After two minutes, the test wells were washed again. The leuco dye composition (50 ml) was added, the devices were incubated at room temperature for 2 minutes. Sodium azide solution (0.1%) was added, and the dye on the membranes was visually graded on a density scale of 0 to 10 (highest density). Background readings were obtained from regions on the membrane surrounding the test regions containing the probes.

Gel electrophoresis was carried out by adding the reaction mixture containing amplified target nucleic acid (6 ml) to agarose gels (4%) which had been prestained with ethidium bromide (4 ml, 10 mg/ml). The gels were electrophoresed at about 160 volts/cm for about 1 hour using an electrophoresis buffer (600 ml) containing ethidium bromide (24 ml). The buffer was a mixture of tris(hydroxymethyl)aminomethane, borate and ethylenediaminetetraacetic acid available from Sigma Chemical Co. The resulting bands were compared to molecular weight markers, and the product band intensity was scored (115-mer for HIV-I DNA and 110-mer for β-globin) according to the scale (−, w=, w, w+, +, ++ and +++) with (−) being the weakest signal and (+++) being the strongest signal.

Examples 1–2

Amplification Comparisons

These examples compare the method of this invention for the detection of HIV-I DNA (gag region) with amplification of the same targeted nucleic acid using a standard method taught for example in U.S. Pat. No. 4,965,188 (noted above).

Three Control methods were carried out whereby amplification was done in microfuge tubes. Control A required about 350 seconds for an amplification cycle (Steps B–D), and had the following steps (the time unaccounted for was used in the heating up and cooling down phases of the steps):

Step A: Target strands were denatured at 95° C. for about 30 seconds.

Step B: The denatured strands were cooled to and held at 55° C. for about 30 seconds to cause them to hybridize with the primers.

Step C: The mixture was heated to and held at 70° C. for a period of about 60 seconds to form primer extension products.

Step D: The resulting hybridized products were denatured by heating them to 95° C. over a period of time of about 60 seconds, and maintaining that temperature for about 30 seconds.

Step E: Steps B through D were repeated 31 times.

Step F: Detection of the amplified target HIV-I DNA was carried out in SURECELL™ disposable test devices using the procedure described above.

Control B was similar, requiring about 240 seconds for an amplification cycle, and having the following steps:

Step A: Target strands were denatured at 95° C. for about 15 seconds.

Step B: The denatured strands were cooled to and held at 53° C. for about 30 seconds to cause them to hybridize with the primers.

Step C: The mixture was heated to and held at 68° C. for a period of about 30 seconds to form primer extension products.

Step D: The resulting hybridized products were denatured by heating them to 95° C., and maintaining that temperature for about 15 seconds.

Step E: Steps B through D were repeated 31 times.

Step F: Detection of the amplified target HIV-I DNA was carried out in SURECELL™ disposable test devices using the procedure described above.

In Control C, amplification was carried out using the following steps and an amplification cycle time (steps B–D) of about 130 seconds:

Step A: Target strands were denatured at 95° C. for about 15 seconds.

Step B: The denatured strands were cooled to 65° C. over a period of about 50 seconds.

Step C: The reaction mixture was held at 65° C. for a period of about 15 seconds to form primer extension products.

Step D: The resulting hybridized products were denatured by heating them to 95° C. over a period of time of about 50 seconds, and maintaining that temperature for 15 seconds.

Step E: Steps B through D were repeated 31 times.

Step F: Detection of the amplified target HIV-I DNA was carried out in microfuge tubes as described above.

Example 1 was similar to Control C except that the amplification cycle time was about 100 seconds with Steps B–D having the following times:

Step B: about 49 seconds.

Step C: about 1 second.

Step D: about 49 for heating and 1 second at the temperature.

Example 2 was similarly carried out but test packs were used for the amplification. The amplification cycle time was about 59 seconds with Steps B–D having the following times and temperatures:

Step B: about 9 seconds cooling to 66° C.

Step C: about 40 seconds at 66° C.

Step D: about 9 seconds heating to 94° C., and maintaining the temperature for 1 second.

TABLE I

| Method | Cycle Time (sec) | Copies | Dye Signal Assay | Background |
|---|---|---|---|---|
| Control A | 360 | 500 | 8.5 | 2.5 |
|  |  | 200 | 7.0 | 1.8 |
|  |  | 100 | 5.5 | 1.5 |
|  |  | 50 | 5.5 | 4.0 |
|  |  | 25 | 3.5 | 2.0 |
|  |  | 10 | 2.8 | 2.0 |
|  |  | 0 | 2.0 | 0.5 |
| Control B | 240 | 500 | 8.5 | 2.0 |
|  |  | 200 | 7.5 | 1.3 |
|  |  | 100 | 4.0 | 1.8 |
|  |  | 50 | 5.0 | 4.0 |
|  |  | 25 | 3.5 | 2.0 |
|  |  | 10 | 2.0 | 1.8 |
|  |  | 0 | 1.0 | 0.8 |
| Control C | 130 | 500 | 8.5 | 1.0 |
|  |  | 200 | 7.8 | 0.5 |
|  |  | 100 | 5.8 | 0.3 |
|  |  | 50 | 4.5 | 0 |
|  |  | 25 | 3.0 | 0 |
|  |  | 10 | 2.0 | 0 |
|  |  | 0 | 0.5 | 0 |
| Example 1 | 100 | 500 | 8.5 | 0 |
|  |  | 200 | 7.3 | 0.5 |
|  |  | 100 | 6.0 | 0.5 |
|  |  | 50 | 5.0 | 1.5 |
|  |  | 25 | 3.0 | 0 |
|  |  | 10 | 1.8 | 0 |
|  |  | 0 | 2.5 | 1.0 |
| Example 2 | 59 | 500 | 8.5 | 0 |
|  |  | 200 | 7.0 | 0 |
|  |  | 100 | 6.5 | 0.8 |
|  |  | 50 | 5.0 | 0 |
|  |  | 25 | 3.3 | 0 |
|  |  | 10 | 1.5 | 0 |
|  |  | 0 | 0.5 | 0 |

The amplified products were detected as described above, and the visual density values are shown in Table I above. The signals were evaluated at different numbers of "copies" which refer to the number of targeted nucleic acid molecules per 100 μl of reaction volume. Examples 1–2 demonstrate that a much faster amplification cycle time can be used to provide high density in signal while background is significantly diminished. The Control methods require longer cycle times to obtain dense signals, and, in many cases, exhibit higher backgrounds.

Examples 3 & 4

Amplification and Detection of HIV-I DNA

These examples compare a standard amplification and detection method like the Controls of foregoing examples carried out in microfuge tubes with methods of the present invention carried out with extremely short cycle times in a chemical test pack as described above. The target nucleic acid is HIV-I DNA at two concentrations, $5 \times 10^{-5}$ molar and $1 \times 10^{-16}$ molar. Thirty cycles of amplification were carried out and detection was accomplished either by using capture probes in SURECELL™ test devices or by gel electrophoresis. A Perkin-Elmer Cetus thermocycler (labeled as "DNA Thermal Cycler") was used in the Control method, whereas the thermal processor described in U.S. Ser. No. 452,666 (noted above) was used in the method of this invention.

The Control method had the same steps as for Control A above (in Examples 1–2). Thus, the temperature for Step B was 55° C. and that for Step C was 70° C.

The method of this invention (Example 3) was carried out at 94° C. for each of Steps A and D, 50° C. or 60° C. (49 second cycle only) for Step B, and 70° C. for Step C. The cycle times (Steps B through D) were varied from 49 to 67 seconds.

The method of this invention (Example 4) had the steps shown for Example 1 above whereby the temperature for Steps A and D was 94° C. and that for Steps B and C was 65° C. (except for the assay where cycle time was about 22.5 seconds, when the denaturation temperature was 92° C.).

The results are provided in Table II below. It is apparent that the method of this invention provided highly sensitive polymerase chain reaction amplification even with very short cycle times, whereas the known control method required a much longer time and more manipulation of temperature settings.

TABLE II

| | | RESULTS | | | |
|---|---|---|---|---|---|
| | Cycle | $5 \times 10^{-5}$ Molar | | $1 \times 10^{-16}$ Molar | |
| Method | Time (sec) | Gel* | Probe** | Gel* | Probe** |
| Control | 360 | ++ | 9.0 | + | 7.0 |
| Example 3 | 67 | ++ | 8.7 | + | 7.0 |
| | 57 | ++ | 8.7 | + | 7.0 |
| | 49 | ++ | 8.7 | + | 6.5 |
| Example 4 | 50 | ++ | 8.7 | + | 7.3 |
| | 40 | ++ | 7.8 | + | 7.0 |
| | 30 | ++ | 8.8 | + | 7.0 |
| | 22.5 | + | 7.8 | W= | 2.7 |

*Detection using gel electrophoresis
**Detection in SureCell ™ test device using capture probe.

Example 5

Comparison Assays Using Test Packs

This comparative example is similar to Example 4 except that all assays were carried out using polymerase chain reaction in test packs and the amplification equipment as described in U.S. Ser. No. 452,666 (noted above). Two targeted nucleic acids were detected: M13/HIV-I DNA ($5 \times 10^{-5}$ molar) and HUT 78 cell line DNA (5000 copies/ml). Thirty cycles of amplification were carried out.

The Control method was carried out using 94° C. for denaturation, 53° C. for the annealing step and 68° C. for primer extension. The method of this invention was carried out at several temperatures (first temperature in the column is for Steps A and D, and the second temperature is for Steps B and C) shown in Table III below.

TABLE III

| | | | RESULTS | | | |
|---|---|---|---|---|---|---|
| | Cycle | Cycle$^{(v)}$ | M13HIV-I DNA | | HUT 78 Cell Line | |
| Method | Time (sec) | Temperatures | Gel* | Probe** | Gel* | Probe** |
| Control | 240 | — | +++ | 10.0 | + | 9.5 |
| Example 5 | 31 | 95/62 | +++ | 10.0 | w+ | 7.5 |
| | 23.5 | 94/60 | ++ | 10.0 | w | 7.0 |
| | 22 | 90/60 | ++ | 9.5 | w+ | 6.3 |
| | 21.5 | 94/62.5 | ++ | 10.0 | w | 6.0 |
| | 20 | 94/65 | w+ | 8.0 | w= | 2.5 |
| | 18 | 90/65 | w | 6.5 | -- | 2.7 |
| | 17.5 | 94/69 | --- | 0 | -- | 0 |
| | 15.5 | 90/69 | --- | 0 | -- | 0 |

*Detection using gel electrophoresis
**Detection in Surecell ™ test device using capture probe.
$^{(v)}$First temperature is for denaturation, the second for annealing and primer extension.

The results are shown in Table III, and indicate that the method of this invention can be carried out using amplification cycle times as short as 18 seconds.

Example 6

Comparative Example Using Different Amounts of Thermostable DNA Polymerase

This example is similar to that of Example 4 and compares assays carried out using both microfuge tubes and long cycle times, and chemical test packs and short cycle times. Also compared were various levels of thermostable DNA polymerase in both microfuge tubes and chemical test packs.

The targeted nucleic acid was HIV-I DNA from the gag region present at a concentration of about 5000 copies/100 µl. Amplification was carried out using 36 cycles in each assay, and detection of the amplified products was accomplished either by measuring dye signal (as described above) with water insoluble capture probes in a SURECELL™ test device or by agarose gel electrophoresis. A commercially available instrument (labeled as "DNA Thermal Cycler", available from Perkin Elmer Cetus) was used for the amplification procedures using the microfuge tubes whereas a thermal cycler described above in U.S. Ser. No. 452,666 was used with the chemical test packs. Table IV below indicates the levels of thermostable DNA polymerase used.

All of the Control assays carried out in tubes were carried out like Control B described above in Examples 1–2, except that Steps A and D were performed at 94° C. Also in these Control assays: Steps B through D were repeated 35 times (Step E), Step A required 15 seconds, Step D required 60 seconds to get to the desired temperature which was then maintained for another 15 seconds, Step B required 30 seconds and Step C required 30 seconds. The total cycle time for the Control assays was about 240 seconds per cycle with heating and cooling temperatures being as fast as the thermocycler equipment could perform.

In the assays of the present invention, Steps A through D were carried out as described in Example 2 with Steps B through D being repeated 35 times. Steps A and D were performed at 94° C. and each required about 11 seconds to reach the temperature which was maintained for an additional 3 seconds. Step B required about 11 seconds to cool the reaction mixture to 65° C. Step C for primer extension product formation was carried out at the same temperature for 5 seconds. The total time for each cycle was about 30 seconds. The assays carried out in chemical test packs using low amounts of DNA polymerase were also performed using the 30 second cycle times, but as the results indicate, the fast cycle time was insufficient to provide the desired results alone.

The results presented in Table IV below indicate that the amplified targeted nucleic acid was detectable using either capture probes (measuring dye signal) or gel electrophoresis using the same results scoring described above. Moreover, assays using fast cycling times provided acceptable detection of amplified products only at DNA polymerase concentrations greater than 6 units/100 µl. The faster cycle times at lower DNA polymerase concentrations provided unacceptable results.

TABLE IV

| Assay | DNA Polymerase (Units/100 µl) | Dye Signal | Electrophoresis Result |
|---|---|---|---|
| Invention (test packs) | 8 | 8.8 | + |
| Invention (test packs) | 6 | 8.3 | + |
| Control (test packs) | 4 | 1.0 | − |
| Control (test packs) | 2 | 3.3 | − |
| Control (test packs) | 1 | 0.5 | − |
| Control (test packs) | 0.5 | 0 | − |
| Control (tubes) | 8 | 7.5 | + |

TABLE IV-continued

| Assay | DNA Polymerase (Units/100 μl) | Dye Signal | Electrophoresis Result |
|---|---|---|---|
| Control (tubes) | 6 | 7.0 | + |
| Control (tubes) | 4 | 8.3 | + |
| Control (tubes) | 2 | 8.3 | + |
| Control (tubes) | 1 | 8.0 | + |
| Control (tubes) | 0.5 | 8.0 | + |

Example 7

Comparison of Amplification Methods Using Different Primer Levels

This example is similar to Example 6 except that all assays were carried out in chemical test packs. The targeted nucleic acid was HIV-I DNA from the HUT cell line and was present at a concentration of 5000 copies/100 μl. The DNA polymerase used was as noted above and was present at a level of 7.5 units/100 μl. The primer concentration was varied from 0.01 to 10 μmolar. Each amplification was carried out with 30 cycles of steps B–D.

The amplification protocol for the Control assays required a cycle time of 160 seconds. The step conditions were the same as in Example 6 except that Steps A and D were performed at 94° C. and each required about 12 seconds to reach that temperature which was maintained for 1 second. Step B required cooling the mixture to 66° C. over a time period of about 12 seconds, and Step C maintained that temperature for 135 seconds. Steps B through D were repeated 29 times.

The amplification method of this invention was performed in identical fashion except that the total cycle time was 38.5 seconds. Steps A and D each required about 9 seconds to reach 94° C., and that temperature was maintained for 1 second. Step B required cooling to 66° C. over about 9 seconds and Step C maintained that temperature for 20 seconds. Steps B through D were repeated 29 times.

An additional amplification was carried out using very low primer concentration, that is 0.01 μmolar using the 38.5 cycle time, but poor results were obtained due to the rapidity of the cycle time.

The results of these assays are presented in Table V below. They indicate that acceptable signal can be obtained using primer concentrations greater than about 0.075 μmolar using the very fast 38.5 second cycle time. The level of primer of 0.1 μmolar did not give acceptable signal in this case, but longer cycle times which are still less than 120 seconds (for example, between 60 and 120 seconds) would likely provide acceptable amplification. The Control assays carried out at 160 seconds provided good signal at all primer concentrations except the lowest. These results also indicate that one skilled in the art should and can readily determine the optimum conditions for a given primer concentration and cycle time to obtain acceptable amplification and detection according to the present invention.

TABLE V

| Assay | Primer Level (μmolar) | Dye Signals Invention | Dye Signals Control | Electrophoresis Invention | Electrophoresis Control |
|---|---|---|---|---|---|
| A | 10 | 9.0 | 9.0 | ++ | ++ |
| B | 1 | 9.0 | 9.0 | ++ | ++ |
| C | 0.1 | 0 | 8.3 | – | W |
| D | 0.01 | 0 | 0 | – | – |

Invention=38.5 seconds per cycle
Controls=160 seconds per cycle

Example 8

Comparison of Primer Concentrations for Amplification Methods

This example is similar to Example 7 except for a few changes in reactants and protocol. All assays were carried out with 30 cycles of Steps B through D. The targeted nucleic acid was β-globin DNA from human placental DNA (Sigma Chemical Co.). The primers were as described above and were present at various levels. HIV-I DNA (HUT cell line present at 5000 copies/100 μl) was also present and amplified in all of the assays using a primer level of 1 μmolar.

In the assays, Steps A and D were each performed at 94° C. requiring about 9 seconds to reach that temperature which was then maintained for 3 seconds. Step B required about 9 seconds to cool the mixture to 66° C. Step C was carried at at the same temperature, but the time for product formation was varied up to 120 seconds for the present invention, and up to 140.5 seconds for the Control assays.

The results in both dye signal and gel electrophoretic results are shown in Table VI below for amplification and detection of the β-globin DNA. It is apparent that a primer level below 0.075 μmolar does not produce acceptable amplification and detection for the present invention using short cycle times. It does produce a signal in the Control assays using undesirably longer cycle times. The primer level of 0.1 μmolar yields acceptable signal at 60.5 second cycle times but not for 40.5 second cycle times. This indicates that within the practice of this invention, one skilled in the art can readily adjust cycle times, primer concentrations and other parameters of the invention to obtain acceptable results using much faster cycle times.

TABLE VI

| Cycle Time (seconds) | Primer Concentration (μmolar) | Results Dye Signal | Results Electro-phoresis |
|---|---|---|---|
| 30.5 | 1.0 | 9.5 | ++ |
| 30.5 | 0.5 | 7.0 | W+ |
| 30.5 | 0.1 | 0 | – |
| 30.5 | 0.05 | 0 | – |
| 40.5 | 1.0 | 10 | +++ |
| 40.5 | 0.5 | 10 | ++ |
| 40.5 | 0.1 | 0 | – |
| 40.5 | 0.05 | 0 | – |
| 60.5 | 1.0 | 10 | +++ |
| 60.5 | 0.5 | 9 | ++ |
| 60.5 | 0.1 | 6.3 | + |
| 60.5 | 0.05 | 0.5 | – |
| 140.5 | 1.0 | 10 | +++ |
| 140.5 | 0.5 | 10 | +++ |
| 140.5 | 0.1 | 9.8 | ++ |
| 140.5 | 0.05 | 9.5 | ++ |

The invention has been described in detail with particular reference to preferred embodiments thereof, but it will be understood that variations and modifications can be effected within the spirit and scope of the invention. All patents, patent applications (published or unpublished, domestic or foreign), scientific literature, books and other prior art cited herein are each incorporated herein by reference for the teaching therein pertinent to this invention.

We claim:

1. A method for the amplification of a nucleic acid comprising the steps of:
   A. heating a targeted double-stranded nucleic acid at a first temperature of about 85 to about 100° C. for about 1 to about 40 seconds to denature the strands of said nucleic acid,
   B. cooling said denatured strands to a second temperature over a time period of about 5 to about 20 seconds,
   C. in the presence of
      1) a thermostable DNA polymerase present in an amount of at least 5 units/100 microliters of solution,
      2) deoxyribonucleoside-5'-triphosphates present in amounts effective for DNA polymerization, and
      3) a set of primers specific for said denatured strands, said primers being present in amounts effective for DNA polymerization,
      forming hybridized primer extension products of said primers and denatured strands by incubating said denatured strands at said second temperature for about 1 to about 80 seconds,
      said second temperature being in the range of about $(T_m-15)°$ C. to about $(T_m+5)°$ C. wherein $T_m$ is the melting temperature of said denatured strands and said primers, and the difference $\Delta T$ between said first and second temperatures being from about 5 to about 45° C.,
   D. heating said hybridized primer extension products to said first temperature over a period of time of about 5 to about 20 seconds and keeping said products at said temperature for about 1 to about 40 seconds, and
   E. repeating steps B through D sequentially as a cycle at least once wherein each cycle of steps B through D is carried out within about 20 to about 120 seconds, provided that if the concentration of each of said primers is less than about 0.075 micromolar the time for each cycle of Steps B through D is at least about 60 seconds.

2. The method of claim 1 wherein heating step A is carried out at a temperature of from about 90 to about 98° C. for from about 1 to about 20 seconds.

3. The method of claim 1 wherein step D is carried out at a temperature of from about 90 to about 98° C., and the time for heating to said temperature is from about 5 to about 10 seconds, and the time of maintaining said temperature is from about 1 to about 15 seconds.

4. The method of claim 1 wherein the second temperature is from about 55 to about 70° C., and step B is carried out for a time of from about 5 to about 15 seconds.

5. The method of claim 1 wherein said second temperature is from about 55 to about 70° C., and step C is carried out for from about 1 to about 40 seconds.

6. The method of claim 1 wherein said DNA polymerase is a thermostable DNA polymerase isolated from a Thermus species or from a genetically engineered equivalent thereof.

7. The method of claim 6 wherein said polymerase is isolated from *Thermus aquaticus, Thermus thermophilus* or *Thermus flavus*, or a genetically engineered equivalent thereof.

8. The method of claim 1 further comprising detection of said primer extension products after step C is performed the last time, either in denatured or undenatured form.

9. The method of claim 1 wherein each cycle of steps B through D is carried out within from about 20 to about 90 seconds.

10. The method of claim 1 wherein each cycle of steps B through D is carried out within from about 30 to about 75 seconds.

11. The method of claim 1 wherein said thermostable DNA polymerase is present at concentration of from about 6 to about 20 units/100 µl of solution.

12. The method of claim 1 wherein the targeted nucleic acid and the reagents of step C are mixed in a volume of from about 50 to about 300 µl.

13. The method of claim 1 wherein $\Delta T$ is from about 20 to about 35° C.

14. The method of claim 1 wherein $\Delta T$ is from about 15 to about 45° C.

15. The method of claim 1 wherein the concentration of each primer is from about 0.1 to about 2 µmolar.

16. A method for the amplification and detection of a nucleic acid comprising the steps of:
   A. heating a targeted double-stranded nucleic acid at a first temperature of about 85 to about 100° C. for about 1 to about 40 seconds to denature the strands of said nucleic acid,
   B. cooling said denatured strands to a second temperature over a time period of about 5 to about 20 seconds,
   C. in the presence of
      1) a thermostable DNA polymerase present in an amount of at least 5 units/100 microliters of solution,
      2) deoxyribonucleoside-5'-triphosphates present in amounts effective for DNA polymerization, and
      3) a set of primers specific for said denatured strands, said primers being present in amounts effective for DNA polymerization,
      forming hybridized primer extension products of said primers and denatured strands by incubating said denatured strands at said second temperature for about 1 to about 80 seconds,
      said second temperature being in the range of about $(T_m-15)°$ C. to about $(T_m+5)°$ C. wherein $T_m$ is the melting temperature of said denatured strands and said primers, and the difference $\Delta T$ between said first and second temperatures being from about 5 to about 45° C.,
   D. heating said hybridized primer extension products to said first temperature over a period of time of about 5 to about 20 seconds and keeping said products at said temperature for from about 1 to about 40 seconds, and
   E. repeating steps B through D sequentially as a cycle at least once wherein each cycle of steps B through D is carried out within about 20 to about 120 seconds,
   F. detecting at least one denatured strand of said nucleic acid, provided that if the concentration of each of said primers is less than about 0.075 micromolar the time for each cycle of Steps B through D is at least about 60 seconds.

17. The method of claim 16 wherein one of said primers is biotinylated, and said detection in step F is carried out by capturing the resulting amplified biotinylated strand using avidin which is attached to a solid substrate, and detecting said captured strand directly or indirectly with a labeled probe.

18. The method of claim 16 wherein one of said primers is biotinylated, and detection in step F is carried out by capturing the resulting amplified biotinylated strand using an insolubilized oligonucleotide complementary thereto, and complexing said biotinylated strand with detectably labeled avidin.

19. The method of claim 16 for the amplification and detection of genomic, bacterial, fungal or viral DNA.

20. The method of claim 19 for the amplification and detection of viral or bacterial DNA.

21. The method of claim 16 for the amplification and detection of viral DNA.

22. The method of claim 21 for the amplification and detection of HIV-I DNA, cytomegaloviral DNA or human papilloma viral DNA.

23. The method of claim 16 for the simultaneous amplification and detection of a plurality of double-stranded nucleic acids using corresponding sets of primers.

24. The method of claim 16 wherein detection in step F is carried out by capturing said denatured strand on a microporous filtration membrane.

25. The method of claim 16 wherein detection in step F is carried out by capturing said denatured strand on a nonporous substrate selected from the group consisting of a polymeric film, a noncoated paper and a polymer coated paper.

26. The method of claim 16 wherein detection is carried out using polymeric particles for insolubilizing said denatured strand.

27. The method of claim 26 wherein each cycle of Steps B through D is carried out within about 30 to about 75 seconds.

28. The method of claim 1 which is carried out in a chemical test pack.

29. The method of claim 1 which is carried out in a reaction tube.

* * * * *

UNITED STATES PATENT AND TRADEMARK OFFICE
CERTIFICATE OF CORRECTION

PATENT NO.     : 6,475,729 B1
DATED          : November 5, 2002
INVENTOR(S)    : Findlay, John B. et al.

It is certified that error appears in the above-identified patent and that said Letters Patent is hereby corrected as shown below:

<u>Title page,</u>
Item [12], delete "Findley" and insert -- Findlay -- therefore.
Item [75], Inventors, "John Bruce Findley", delete "Findley" and insert -- Findlay --

Signed and Sealed this

Twenty-second Day of April, 2003

JAMES E. ROGAN
*Director of the United States Patent and Trademark Office*